United States Patent

(12) United States Patent
Bal

(10) Patent No.: US 9,861,309 B2
(45) Date of Patent: Jan. 9, 2018

(54) GLUCOSE MONITORING SYSTEM AS CONTROL INPUT TO ADJUSTABLE FOCAL LENGTH LENSES

(71) Applicant: FREESCALE SEMICONDUCTOR, INC., Austin, TX (US)

(72) Inventor: Linda M. Bal, Austin, TX (US)

(73) Assignee: NXP USA, Inc., Austin, TX (US)

( * ) Notice: Subject to any disclaimer, the term of this patent is extended or adjusted under 35 U.S.C. 154(b) by 190 days.

(21) Appl. No.: 14/566,952

(22) Filed: Dec. 11, 2014

(65) Prior Publication Data
US 2016/0166200 A1    Jun. 16, 2016

(51) Int. Cl.
| A61B 5/00 | (2006.01) |
| G02C 7/04 | (2006.01) |
| G02C 7/08 | (2006.01) |
| A61B 5/145 | (2006.01) |
| A61B 5/08 | (2006.01) |

(52) U.S. Cl.
CPC ........ *A61B 5/4836* (2013.01); *A61B 5/14532* (2013.01); *A61B 5/7275* (2013.01); *G02C 7/04* (2013.01); *G02C 7/083* (2013.01); *A61B 5/082* (2013.01); *A61B 5/14503* (2013.01); *A61B 5/14517* (2013.01); *A61B 5/7282* (2013.01)

(58) Field of Classification Search
CPC ....... A61B 5/14532; G02C 7/04; G02C 7/083

USPC ................ 600/310, 316, 322, 319; 351/246, 351/159.03, 159.39
See application file for complete search history.

(56) References Cited

U.S. PATENT DOCUMENTS

| 4,750,830 A | 6/1988 | Lee |
| 8,188,880 B1 | 5/2012 | Chi et al. |
| 8,922,366 B1* | 12/2014 | Honore .............. A61B 5/14532 351/158 |
| 2009/0195749 A1 | 8/2009 | Blum et al. |

FOREIGN PATENT DOCUMENTS

WO    2010094008 A1    8/2010

OTHER PUBLICATIONS

Scott, M., "Novartis Joins With Google to Develop Contact Lens That Monitors Blood Sugar", http://www.nytimes.com/2014/07/16/business/international/novartis-joins-with-google-to-develop-contact-lens-to-monitor-blood-sugar.html, Jul. 15, 2014, 2 pages.

* cited by examiner

Primary Examiner — Zachary Wilkes

(57) ABSTRACT

A mechanism to adjust variable focus lenses using monitored glucose levels is provided. A glucose sensor provides current blood glucose levels to a controller for the variable focus lenses. The controller determines appropriate adjustment control information for the variable focus lenses based upon the reported glucose levels. This adjustment control information is provided to the lenses, which are adjusted accordingly.

6 Claims, 3 Drawing Sheets

A1C Levels
(percentage of hemoglobin coated w/sugar)
% of glycated hemoglobin

GLUCOSE MONITORING SYSTEM AS CONTROL INPUT TO ADJUSTABLE FOCAL LENGTH LENSES

BACKGROUND

Field

This disclosure relates generally to adjustable focal length lenses, and more specifically, to use of a glucose monitoring system as a control input to adjustable focal length lenses.

Related Art

Persons who have diabetes can have high blood sugar levels over a prolonged period of time due to either that person's pancreas not producing enough insulin or that person's body not responding properly to the insulin produced. Type 1 diabetes results from a body failing to produce enough insulin, while Type 2 diabetes can begin with insulin resistance. High blood sugar levels can produce a variety of short term symptoms in a diabetic, including, for example, frequent urination, increased thirst, increased hunger, and the like.

Another symptom of fluctuating blood sugar levels in diabetics is fluctuating vision, which can make a single pair of corrective lenses ineffective. Blood sugar levels affect the ability of the eye lens to maintain sharp focus by causing the lens to swell, and thereby changing the curvature of the lens. In some cases, when blood sugar is high, near vision can be good and distance vision can deteriorate. On the other hand, when blood sugar is low, near vision can deteriorate and distance vision can improve.

Variable focus lenses can be used to adjust a prescription for fluctuating eyesight. Such lenses provide a mechanical mechanism for changing the prescription (e.g., injection of a fluid into a chamber containing an elastic membrane between two lenses to alter curvature of the membrane, or changing a relationship between two lenses) or an electronic mechanism for changing the prescription (e.g., liquid crystals and the like). But traditional mechanisms require manual adjustment of the lens focus, which can be bothersome and interrupts normal activities.

BRIEF DESCRIPTION OF THE DRAWINGS

The present invention may be better understood, and its numerous objects, features, and advantages made apparent to those skilled in the art by referencing the accompanying drawings.

The use of the same reference symbols in different drawings indicates identical items unless otherwise noted. The figures are not necessarily drawn to scale.

DETAILED DESCRIPTION

Embodiments of the present invention provide a mechanism to adjust variable focus lenses using monitored glucose levels. A glucose sensor provides current blood glucose levels to a controller for the variable focus lenses. The controller determines appropriate adjustment control information for the variable focus lenses based upon the reported glucose levels. This adjustment control information is provided to the lenses, which are adjusted accordingly.

Continuous glucose monitoring (CGM) is a system by which blood glucose levels are tracked day and night. Periodically (e.g., every five minutes), the CGM system collects glucose readings, storing them for analysis of trends and patterns. A typical CGM system uses a transcutaneous analyte sensor that is placed under the skin. A transmitter on the sensor can wirelessly transmit glucose measurement information to a receiver that provides the glucose measurement information to a monitor that can display and store the data. Typically, the collected information can help a person with diabetes (and their physician) to record low overnight blood sugar levels, track high blood sugar levels between meals, detect early morning spikes in blood sugar, and evaluate how diet and exercise affect blood sugar levels.

CGM systems use a variety of sensors to detect blood glucose levels. As stated above, one type of sensor is a transcutaneous analyte sensor, where the sensor is implanted beneath the skin. Another type of blood glucose sensor can detect glucose levels in tears through a sensor incorporated into a contact lens, or can detect glucose levels through sweat. Another type of blood glucose sensor can detect acetone levels in a person's breath. Breath acetone is correlated with blood glucose level. Embodiments of the present invention are not limited to the nature of the blood glucose sensor or associated monitoring system.

A diabetic's eyesight is correlated to their blood glucose level. As discussed above, the ability of the muscles in the eye to vary the shape of an eye's lens is tied, at least in part, to the level of blood glucose. As glucose levels increase, the lens can swell, thus affecting not only the focal length of the lens, but also the eye's natural ability to change that focal length for near and distance vision.

Figure 1:
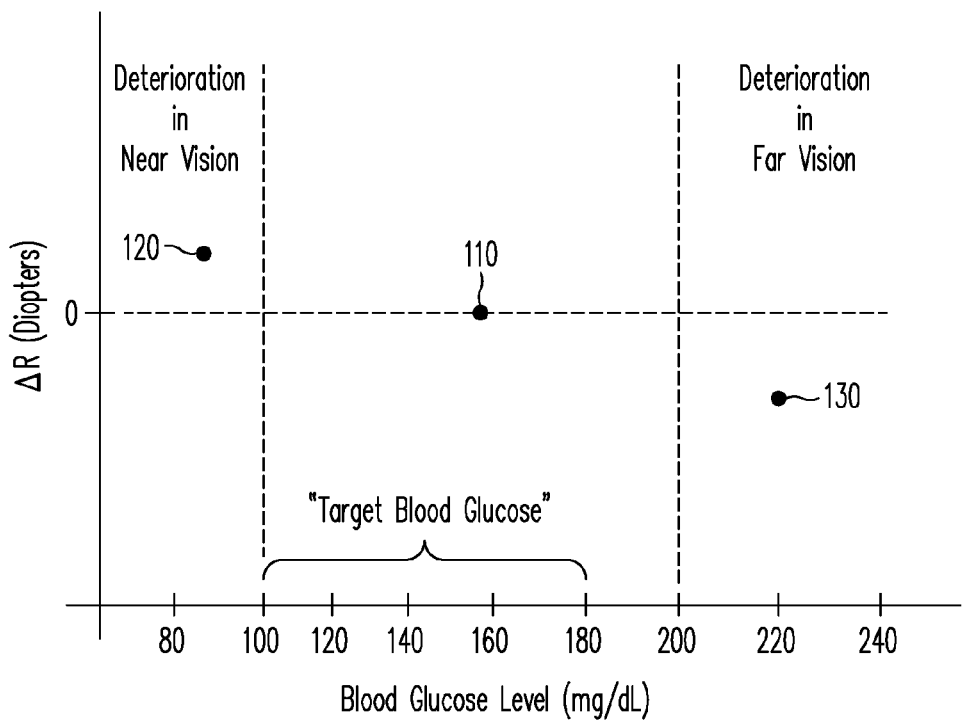
FIG. 1 is a simplified chart illustrating a relative effect of blood glucose levels on corrective lens prescription.

FIG. 1 is a simplified chart illustrating a relative effect of blood glucose levels on corrective lens prescription. One measure of blood glucose levels is milligrams of glucose in a deciliter of blood. A "target" range of blood glucose for a diabetic is in the region of 100 (before eating)-180 mg/dL (after eating). A diabetic's blood glucose level can drop below 100 mg/dL after, for example, prolonged periods of not eating (e.g., in the morning after waking up) or exercise. In addition, after eating, a diabetic's blood glucose level can rise above 200 mg/dL. These low and high blood glucose ranges can have a variety of effects on a diabetic's body.

As discussed above, blood glucose levels have an effect on the ability of the eye to focus. FIG. 1 illustrates this as a relative change in vision from that measured in the "target" blood glucose range. Thus, vision data point 110 is at a zero relative change.

Low blood glucose can have an effect of deteriorating near vision focus. Thus, there can be a relative increase in a lens diopter to correct vision for a person with low blood glucose, as represented by vision data point 120. High blood glucose, on the other hand, can have an effect of deteriorating distance vision. Thus, there can be a relative decrease in lens diopter to correct vision for a person with high blood glucose, as represented by vision data point 130. The actual relative changes in vision in the low and high blood glucose ranges vary from person to person, just as the need for vision correction varies from person to person. In order to determine the actual relative vision correction changes, a diabetic's eyesight would be measured in each of the low, high, and target ranges for blood glucose.

Some diabetics may not have blood glucose levels that typically swing from low to target to high, as suggested by FIG. 1. They may have typical blood glucose levels that remain high during the day and spike higher after meals. One measurement of typical blood glucose levels is characterized by an A1C test (also known as a glycated hemoglobin or glycosylated hemoglobin test).

Figure 2:
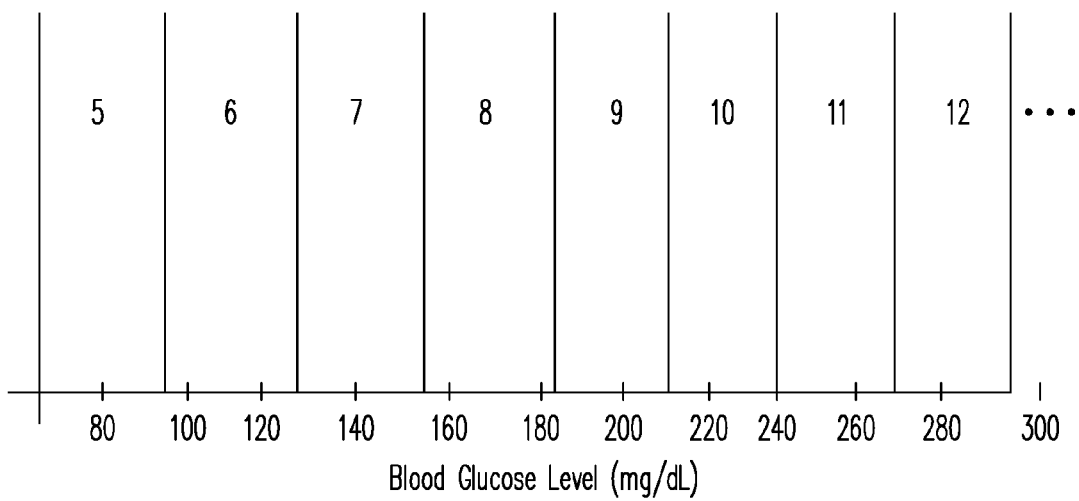
FIG. 2 is an example of A1C levels representing a percentage of glycated hemoglobin.

FIG. 2 is an example of A1C levels. Each A1C level represents a percentage of glycated hemoglobin, or hemoglobin coated with sugar. Thus, a person having an A1C level of 8 means that 8% of that person's blood hemoglobin is coated with sugar. A "normal" person typically has an A1C level of 6 or less. If a person has an A1C level of 8 or higher, this would mean that their blood glucose levels are typically in the high range. Therefore, their eyesight may experience ranges of deterioration in distance vision (e.g., decreasing lens diopter for higher levels of blood glucose level). Thus, for such individuals, a set of vision measurements would be made throughout their expect high blood glucose levels, but only a few, or one, measurements made at a lower blood glucose level.

Figure 3:
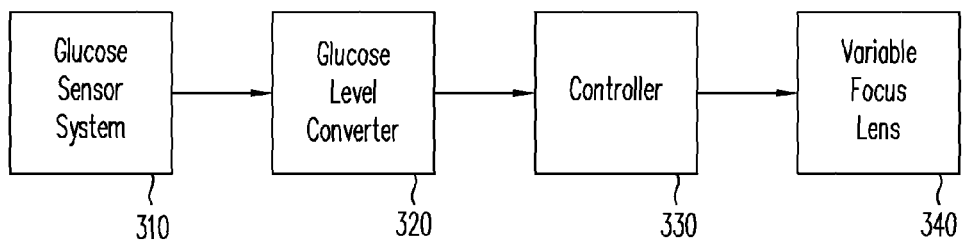
FIG. 3 is a simplified block diagram illustrating a system for adjusting a variable focus lens in light of measured blood glucose levels.

FIG. 3 is a simplified block diagram illustrating a system 300 for adjusting a variable focus lens in light of measured blood glucose levels, in accord with embodiments of the present invention. A blood glucose sensor system 310 is used to detect the blood glucose level of the person needing vision correction. Embodiments of the present invention can use periodic or continuous blood glucose measurement information. As discussed above, glucose sensor system 310 can include a continuous glucose monitoring system (CGM) that is configured to track blood glucose levels day and night, either continuously or periodically. Such CGM systems include a sensor that is either inserted under a diabetic patient's skin or otherwise attached to the diabetic patient in a manner suitable for the type of glucose sensor. For example, blood glucose can be measured in tears or in the patient's breath. Measuring blood glucose in tears can be performed by a sensor coupled to a contact lens, for instance. Alternatively, a subcutaneous blood glucose sensor can transmit sensor data to a receiving unit that is part of the CGM system either wirelessly or via transcutaneous wires. The receiving unit can subsequently use that sensor data to calculate current blood glucose levels.

The current blood glucose levels can be provided from glucose sensor system 310 to a glucose level converter 320. Glucose level converter 320 modifies the current blood glucose level data to data that can be used as inputs for controller 330 of variable focus lens 340. In addition, glucose level converter 320 can process data received from glucose sensor system 310 in a manner that is best for the optical correction device as well as minimizes inconvenience to the user of the optical correction device.

In one embodiment, glucose level converter 320 can change the optics at discrete intervals. As discussed above, prescriptions for eye correction can be determined using typical optometric evaluation at specified glucose levels (e.g., at least two glucose levels). Threshold levels for adjusting the variable focus optical correction device in response to glucose levels can be set for both rising and falling glucose levels, or can be the same for both rising and falling glucose levels. The more glucose level-to-optical prescription data points that are available to the glucose level converter, the better the system can respond to how vision changes. Control data expected by the variable focus lens is generated at each threshold, and then provided to controller 330.

In another embodiment, glucose level converter 320 can change the optics in a continuous manner. As with the previous embodiment, eye correction prescriptions at a variety of blood glucose levels can be determined through traditional optometric evaluation. A sufficient number of prescription data points are determined so that a prescription curve can be developed through curve fitting. Such a prescription curve can thereby capture the full complexity of how the diabetic patient's vision changes over the range of experienced glucose levels. The glucose level converter can then determine the appropriate control information for the optical correction device for all glucose levels in the range experienced by the diabetic patient. But to reduce an annoyance of having a continuously changing prescription, adjustments to the control information provided to the optical correction device can be made when a current glucose level has a change over a glucose level for a previously set prescription larger than a predetermined threshold. Once the threshold change has been reached, a new set of control information can be provided to controller 330 in light of the optical prescription at that glucose level.

Controller 330 receives the control data and adjusts the optical correction device 340, accordingly. For example, for variable focal length eyeglasses having a deformable membrane to adjust focal length, controller 330 can provide control signals to a motor that provides pressure to adjust the deformable membrane. The control signals will deform the membrane to provide a focal length associated with the user's needed vision correction for the measured blood glucose level. As another example, for variable focal length eyeglasses incorporating liquid crystal technology to adjust focal length, the controller can provide appropriate control information to electrically modify the orientation of the liquid crystals in the lenses to provide a focal length associated with the user's needed vision correction for the measured blood glucose level. As a further example, for variable focal length contact lenses, the controller can provide appropriate control information to the lenses to deform the lenses to provide a focal length associated with the user's needed vision correction for the measured blood glucose level. For such contact lenses, the controller can be formed on the lenses themselves, along with the deformation mechanism. The glucose level converter can communicate wirelessly with the controller to provide the control data.

Figure 4:
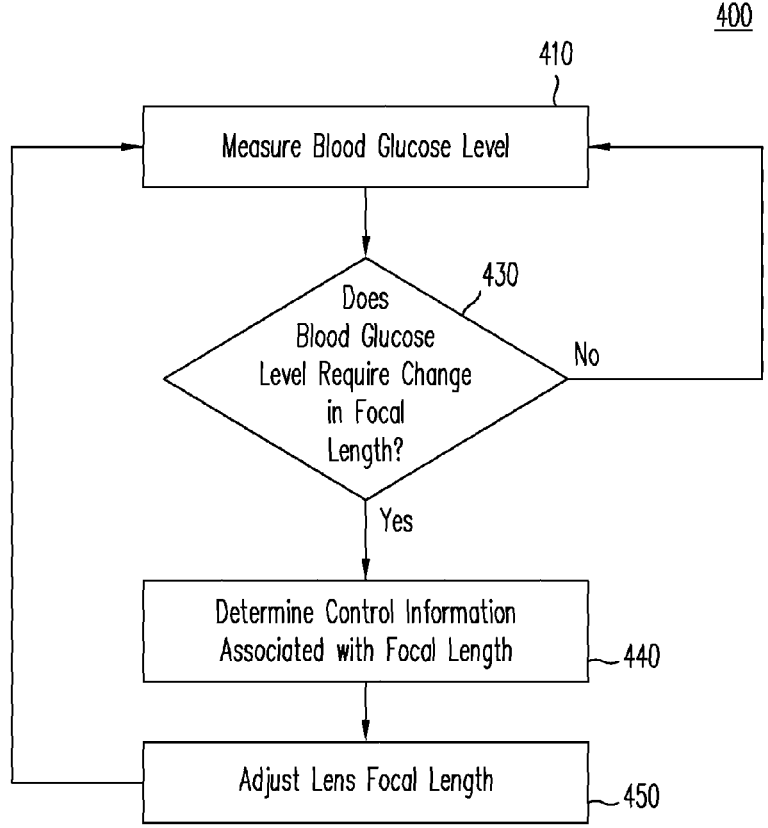
FIG. 4 is a simplified flow diagram illustrating a method used by embodiments of the present invention to adjust focal length of adjustable focal length lenses in response to measured blood glucose levels.

FIG. 4 is a simplified flow diagram illustrating a method 400 used by embodiments of the present invention to adjust focal length of adjustable focal length lenses in response to measured blood glucose levels. Blood glucose levels are measured continuously by an appropriate sensor (410). As discussed above, such sensors can vary in their nature depending upon how one wishes to measure blood glucose (e.g., subcutaneously, through tears, and the like). The blood glucose level information is used in determining whether to change the focal length of variable focal length lenses.

Figure 5:
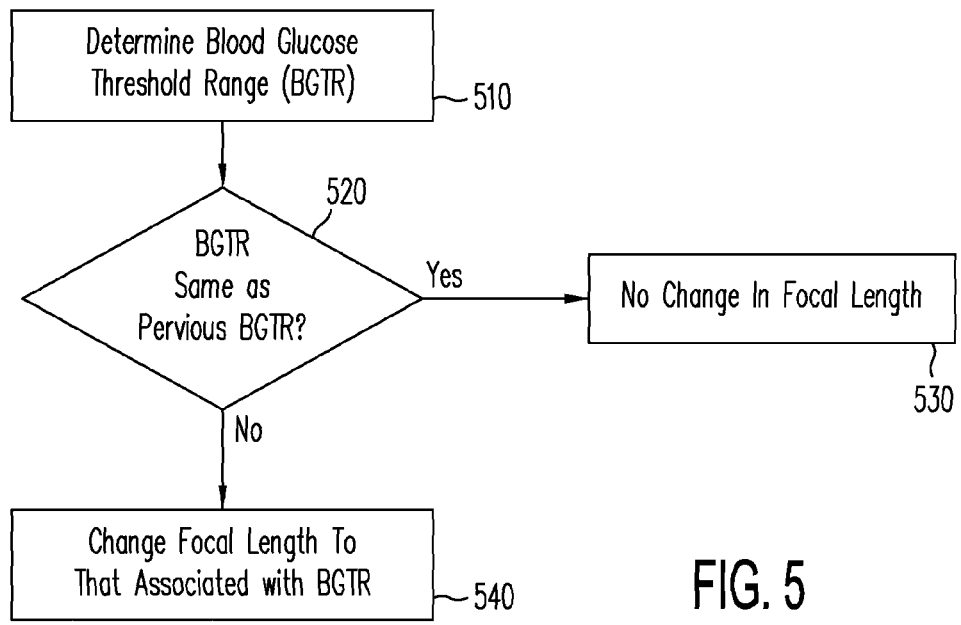
FIG. 5 is a simplified flow diagram illustrating a method usable by embodiments of the present invention to determine a focal length associated with a threshold range of blood glucose levels.

The blood glucose level information can be provided to the glucose level converter, for example, and a determination is made as to whether the measured blood glucose level requires a change in the lens focal length (430). Such a determination can be made in a variety of ways, depending upon the application. In one embodiment, as illustrated in FIG. 5, threshold ranges can be associated with each measured focal length/blood glucose relationship. A determination is made as to whether the measured blood glucose level is within a predetermined threshold range (510), and if the predetermined range is the same as that associated with a previous measurement (520), then the blood glucose level suggests no change in focal length of the lenses (530). If the predetermined range is different from that associated with the previous measurement, then the blood glucose level suggests a change in focal length of the lenses (540). In some embodiments, a rising threshold and a descending threshold can be different between two threshold ranges (e.g., rising threshold set higher than the descending threshold). This sets up a hysteresis that avoids a constant switching between focal lengths at a borderline blood glucose level.

Figure 6:
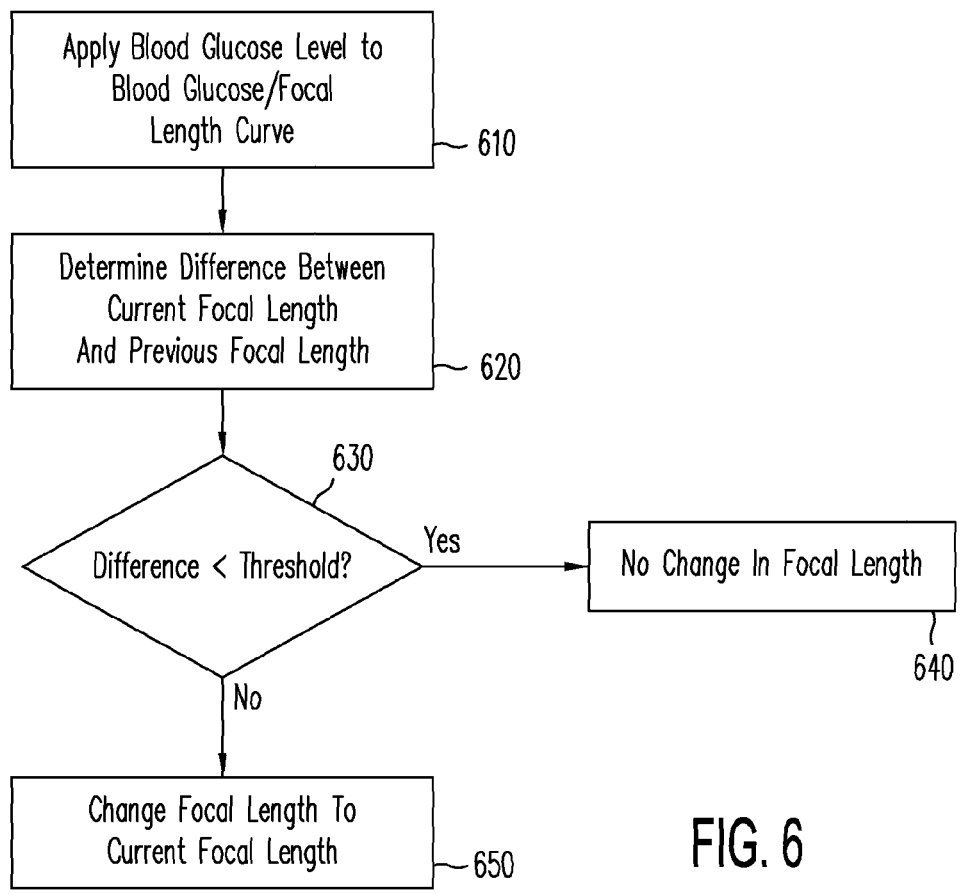
FIG. 6 is a simplified flow diagram illustrating a method usable by embodiments of the present invention to determine whether to adjust to a focal length associated with a measured blood glucose level.

In another embodiment, as illustrated in FIG. 6, eye correction focal lengths can be determined through normal optometric evaluation and a sufficient number of glucose levels such that a curve can be matched to the data points. This curve can capture the complexity of how the user's vision changes over glucose levels normally experienced by the user. Continuous monitoring of blood glucose levels can then be applied to the curve to determine a focal length for any blood glucose level (610). To reduce an annoyance factor of a continuously changing prescription, an adjustment to focal length can be made when a previously set focal length has a measured differential greater than a predetermined threshold over the currently determined focal length. A determination is made of the difference between the focal length associated with the current blood glucose level and the previously set focal length (620). If the difference is less than a predetermined threshold for changing the focal length (630), then no change in the focal length is indicated (640). If, however, the difference is greater than the predetermined threshold for change, then a change in focal length to that associated with the current blood glucose level is indicated (650). It should be noted that there can be many variations of how to determine when to alter a previously set focal length, and that the scope of the present invention is not limited to any particular embodiment.

If determination 430 is that the measured blood glucose level does not require a change in focal length of the adjustable focal length lenses, then the system can wait a length of time appropriate to the application to measure the next blood glucose level (e.g., five minutes). If the determination 430 is that the measured blood glucose level does require a change in focal length of the adjustable focal length lenses, then a determination is made of the control information for the lens associated with the desired focal length (440). This information is provided to the lens controller, so that the lens can be physically adjusted, as discussed above (450). The system then returns to waiting for the next measured blood glucose value.

By now it should be appreciated that there has been provided a system for adjusting a variable focal length lens in response to blood glucose levels. In one embodiment, the system includes a glucose sensor system, a glucose level converter, and a controller for the variable focal length lens. The glucose level converter is coupled to the glucose sensor system and the controller for the variable focal length lens, and is configured to provide a current set of control information to the controller in response to blood glucose information received from the glucose sensor system.

In one aspect of the above embodiment, the glucose sensor system includes an analyte sensor configured to detect blood glucose levels and provide information regarding the detected blood glucose levels, and a transmitter configured to receive the information regarding the detected blood glucose levels from the analyte sensor and to transmit corresponding blood glucose information to the glucose level converter. In a further aspect, the analyte sensor is one of a transcutaneous analyte sensor, a sensor configured to detect glucose levels in tears, a sensor configured to detect acetone levels in breath, or a sensor configured to detect glucose levels in sweat.

In another aspect, the glucose sensor system is configured to periodically provide blood glucose information. In a still further aspect, the glucose level converter is further configured to: determine a blood glucose level associated with the blood glucose information; select a current range of blood glucose levels with which the blood glucose level is associated, where the current range of blood glucose levels is selected from a stored set of predetermined ranges of blood glucose levels; and, determine the current set of control information for the variable focal length lens, if the current range of blood glucose levels is different from an immediately previously selected range of blood glucose levels, where the current set of control information is associated with the current range of blood glucose levels. In a still further aspect, the current set of control information is associated with a focal length of the variable focal length lens. In a further aspect, the focal length of the variable focal length lens is associated with an optical prescription for a user of the system when the user's blood glucose level is within the current range of blood glucose levels.

In another aspect, the glucose sensor system is configured to continuously provide blood glucose information. In a further aspect, the glucose level converter is further configured to determine a blood glucose level associated with the blood glucose information, determine a current focal length using the blood glucose level, and determine the current set of control information for the variable focal length lens using the current focal length. In a still further aspect the glucose level converter is configured to determine the current focal length by virtue of being further configured to determine the current focal length using a predetermined function derived from a set of measurements of optical prescription in light of blood glucose level for a user of the system and the blood glucose level. In a further aspect, the glucose level converter is configured to determine the current set of control information for the variable focal length lens by virtue of being further configured to determine a difference between the current focal length and an immediately previously set focal length, and determine the current set of control information for the variable focal length lens using the current focal length if a magnitude of the difference between the current focal length and the immediately previously set focal length is greater than a predetermined threshold.

Another aspect includes the variable focal length lens, which is coupled to the controller for the variable focal length lens.

Another embodiment provides a method for adjusting a variable focal length lens in response to blood glucose levels. The method includes measuring a current blood glucose level, determining if the current blood glucose level requires a change in focal length of the variable focal length lens, and determining a current set of control information for the variable focal length lens if the current blood glucose level requires a change in the focal length.

In one aspect of the above embodiment, measuring the current blood glucose level includes detecting the blood glucose level using an analyte sensor, and transmitting the blood glucose information corresponding to the detected blood glucose level to a glucose level converter. In a further aspect, measuring the current blood glucose level includes periodically performing the transmitting of the blood glucose information. In a yet further aspect, determining if the current blood glucose level requires a change in focal length further includes determining a blood glucose level associated with the blood glucose information, selecting a current range of blood glucose levels with which the blood glucose level is associated from a set of predetermined ranges of blood glucose levels, and determining the current set of control information for the variable focal length lens from the current range of blood glucose levels if the current range of blood glucose levels is different from an immediately previously selected range of blood glucose levels. In a further aspect, the current set of control information is associated with a focal length of the variable focal length lens.

In another aspect, measuring the current blood glucose level includes continuously transmitting the blood glucose information. In a further aspect, determining if the current blood glucose level requires a change in focal length further includes determining a blood glucose level associated with the blood glucose information, determining a current focal length using the blood glucose level using a predetermined function derived from a set of measurements of optical prescription in light of blood glucose level for a user of the system, and determining the current set of control information for the variable focal length lens using the current focal length. In another aspect, determining the set of control information further includes determining a difference between the current focal length and an immediately previously set focal length, and determining the current set of control information for the variable focal length lens using the current focal length if the magnitude of the difference between the current focal length and the immediately previously set focal length is greater than a predetermined threshold.

Because the apparatus implementing the present invention is, for the most part, composed of electronic components and circuits known to those skilled in the art, circuit details will not be explained in any greater extent than that considered necessary as illustrated above, for the understanding and appreciation of the underlying concepts of the present invention and in order not to obfuscate or distract from the teachings of the present invention.

Some of the above embodiments, as applicable, may be implemented using a variety of different information processing systems. For example, although FIG. 3 and the discussion thereof describe an exemplary information processing architecture, this exemplary architecture is presented merely to provide a useful reference in discussing various aspects of the invention. Of course, the description of the architecture has been simplified for purposes of discussion, and it is just one of many different types of appropriate architectures that may be used in accordance with the invention. Those skilled in the art will recognize that the boundaries between logic blocks are merely illustrative and that alternative embodiments may merge logic blocks or circuit elements or impose an alternate decomposition of functionality upon various logic blocks or circuit elements.

Thus, it is to be understood that the architectures depicted herein are merely exemplary, and that in fact many other architectures can be implemented which achieve the same functionality. In an abstract, but still definite sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

Also for example, in one embodiment, the illustrated elements of system 300 are circuitry located on a single integrated circuit or within a same device. Alternatively, system 300 may include any number of separate integrated circuits or separate devices interconnected with each other.

Furthermore, those skilled in the art will recognize that boundaries between the functionality of the above described operations merely illustrative. The functionality of multiple operations may be combined into a single operation, and/or the functionality of a single operation may be distributed in additional operations. Moreover, alternative embodiments may include multiple instances of a particular operation, and the order of operations may be altered in various other embodiments.

A computer system processes information according to a program and produces resultant output information via I/O devices. A program is a list of instructions such as a particular application program and/or an operating system. A computer program is typically stored internally on computer readable storage medium or transmitted to the computer system via a computer readable transmission medium. A computer process typically includes an executing (running) program or portion of a program, current program values and state information, and the resources used by the operating system to manage the execution of the process. A parent process may spawn other, child processes to help perform the overall functionality of the parent process. Because the parent process specifically spawns the child processes to perform a portion of the overall functionality of the parent process, the functions performed by child processes (and grandchild processes, etc.) may sometimes be described as being performed by the parent process.

Although the invention is described herein with reference to specific embodiments, various modifications and changes can be made without departing from the scope of the present invention as set forth in the claims below. For example, the adjustable lenses can be a variety of types. Accordingly, the specification and figures are to be regarded in an illustrative rather than a restrictive sense, and all such modifications are intended to be included within the scope of the present invention. Any benefits, advantages, or solutions to problems that are described herein with regard to specific embodiments are not intended to be construed as a critical, required, or essential feature or element of any or all the claims.

The term "coupled," as used herein, is not intended to be limited to a direct coupling or a mechanical coupling.

Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles.

Unless stated otherwise, terms such as "first" and "second" are used to arbitrarily distinguish between the elements such terms describe. Thus, these terms are not necessarily intended to indicate temporal or other prioritization of such elements.

What is claimed is:

1. A system for adjusting a variable focal length lens in response to blood glucose level, the system comprising:
   a glucose sensor system, configured to continuously provide blood glucose information, and comprising
      an analyte sensor configured to detect blood glucose levels and provide information regarding the detected blood glucose levels, and
      a transmitter configured to receive the information regarding the detected blood glucose levels from the analyte sensor and to transmit corresponding blood glucose information to a glucose level converter;
   the glucose level converter, coupled to the glucose sensor system and a controller for the variable focal length lens, and configured to
      determine a blood glucose level associated with the blood glucose information received from the glucose sensor system,
      determine a current focal length using the blood glucose level where determining the current focal length comprises using the blood glucose level and a predetermined function derived from a set of measurements of optical prescription in light of blood glucose level for a user of the system,
      determine the current set of control information for the variable focal length lens using the current focal length, and
      provide the current set of control information to the controller.

2. The system of claim 1 wherein the analyte sensor comprises one of a transcutaneous analyte sensor, a sensor configured to detect glucose levels in tears, a sensor configured to detect acetone levels in breath, or a sensor configured to detect glucose levels in sweat.

3. The system of claim 1 wherein the glucose level converter is configured to determine the current set of control information for the variable focal length lens by being further configured to
   determine a difference between the current focal length and an immediately previously set focal length;
   determine the current set of control information for the variable focal length lens using the current focal length, if a magnitude of the difference between the current focal length and the immediately previously set focal length is greater than a predetermined threshold.

4. The system of claim 1 further comprising:
   the variable focal length lens, wherein the variable focal length lens is coupled to the controller for the variable focal length lens.

5. A method for adjusting a variable focal length lens in response to blood glucose levels, the method comprising:
   measuring a current blood glucose level said measuring comprising detecting the blood glucose level using an analyte sensor and continuously transmitting blood glucose information corresponding to the detected blood glucose level to a glucose level converter;
   determining if the current blood glucose level requires a change in focal length of the variable focal length lens, comprising
   determining a blood glucose level associated with the blood glucose information, and
   determining a current focal length using the blood glucose level using a predetermined function derived from a set of measurements of optical prescription in light of blood glucose level for a user of the system;
   determining a current set of control information for the variable focal length lens, if the current blood glucose level requires a change in focal length, and adjusting the variable focal length lens based on the set of control information.

6. The method of claim 5 wherein determining the set of control information further comprises:
   determining a difference between the current focal length and an immediately previously set focal length;
   determining the current set of control information for the variable focal length lens using the current focal length, if a magnitude of the difference between the current focal length and the immediately previously set focal length is greater than a predetermined threshold.

* * * * *